| United States Patent [19] | [11] | 4,164,419 |
|---|---|---|
| Kaji et al. | [45] | Aug. 14, 1979 |

[54] POWDERED ALLOY FOR DENTAL AMALGAM

[75] Inventors: Hiroyuki Kaji; Narishige Suzuki, both of Kyoto, Japan

[73] Assignee: Shofu Dental Manufacturing Company, Limited, Kyoto, Japan

[21] Appl. No.: 890,307

[22] Filed: Mar. 27, 1978

Related U.S. Application Data

[63] Continuation of Ser. No. 742,454, Nov. 17, 1976, abandoned.

[30] Foreign Application Priority Data

Dec. 22, 1975 [JP] Japan .................................. 50-153664

[51] Int. Cl.$^2$ ............................ C22C 7/00; C22C 5/06
[52] U.S. Cl. ................................... 75/169; 75/0.5 R; 75/134 B; 75/134 C; 75/173 C; 75/251
[58] Field of Search ............ 75/173 C, 134 C, 134 B, 75/134 N, 169, 0.5 R, 251, 255

[56] References Cited

U.S. PATENT DOCUMENTS

| 1,959,668 | 5/1934 | Grey | 75/169 |
|---|---|---|---|
| 3,305,356 | 2/1967 | Youdelis | 75/173 C |
| 3,440,039 | 4/1969 | Watson | 75/134 N |
| 3,591,370 | 7/1971 | Denereaz | 75/173 C |
| 3,871,876 | 3/1975 | Asgar et al. | 75/173 C |
| 3,975,192 | 8/1976 | Simpson | 75/173 C |
| 3,985,558 | 10/1976 | Simpson | 75/134 N |

FOREIGN PATENT DOCUMENTS

50-147412  11/1975  Japan .

OTHER PUBLICATIONS

MacCulloch, "The Effects of Adding Indium to Dental Amalgams," British Dental Journal, vol. 123, No. 11, 12/5/67, pp. 519–525.

*Primary Examiner*—Arthur J. Steiner
*Attorney, Agent, or Firm*—Karl F. Ross

[57] ABSTRACT

A dental alloy capable of combination with mercury to form a dental amalgam comprising by weight 20% and above silver, 20 to 50% tin, 9.5 to 50% copper, and 0.5% and above indium.

4 Claims, No Drawings

POWDERED ALLOY FOR DENTAL AMALGAM

This is a continuation of application Ser. No. 742,454, filed 17 Nov. 1976, now abandoned.

FIELD OF THE INVENTION

This invention relates to dental alloys capable of combination with mercury to form a dental amalgam which comprises by weight 20% and above silver, 20 to 50% tin, 9.5 to 50% copper, and 0.5% and above indium. More particularly, the invention relates to such alloys comprising 20% and above silver, 20 to 50% tin, 11 to 20% copper and 0.5% and above indium.

BACKGROUND OF THE INVENTION

The requirements for dental alloys include adequate working time in which to fill the tooth cavity as well as to carve the tooth's surfaces to conform to dental anatomy, good handling properties, minimum dimensional changes with lapse of time, sufficient mechanical and physical properties to permit normal biting and chewing over a long period of time, and finally superior tarnish and corrosion resistance.

The American Dental Association has set qualitative and quantitative elemental restrictions for amalgam alloys in its Specification No. 1 (Revised), which include in weight percentages 65% or more silver, 29% or less tin, 6% or less copper, 2% or less zinc and 3% or less mercury. While alloys made under said specification are adequate, they exhibit relatively low mechanical properties, and are corrosion prone.

To improve mechanical properties of amalgam alloys, it has been proposed to admix an adequate supply of copper-silver eutetic particles with the alloy made in accordance with said Specification. When such a high-copper alloy is mixed with mercury, and the resultant amalgam microscopically analyzed, there are many non-reacted silver-tin particles dispersed in the matrix which advantageously affect the mechanical properties of the amalgam. U.S. Pat. No. 3,305,356 discloses an example of such a high-copper alloy for amalgam.

Although an amalgam with such a high copper content has improved mechanical properties, it has lower tarnish resistance to oral sulfides. Although the physical and mechanical properties of the amalgam are not affected by tarnish, the latter can seriously affect aesthetics and even possibly health.

In order to improve upon both the mechanical and chemical properties and tarnish resistance of dentral amalgams, we previously developed a group of alloys containing silver, copper, tin and indium (c.f., Japanese Patent No. SHO 50-147412), which was superior to the prior art alloys in mechanical properties and tarnish resistance. However, we have now found a composition range of such alloys surprisingly superior to the alloys of the Japanese Patent.

The prior art includes other amalgamating alloys that contain indium. For example U.S. Pat. No. 1,959,668 to Gray discloses dental alloys which comprise silver, tin, and relatively small amounts of tin and copper and up to 25% by weight indium. Additional prior art which discloses dental alloys which contain indium includes *British Dental Journal: The Effects of Adding Indium to Dental Amalgams*, MacCulloch, vol. 123, No. 11 (12/5/67). None of the dental alloys disclosed therein, however, has satisfactory compressive strength or workability. None of these references discloses dental alloys which contain both indium and copper wherein the weight percent of the latter is more than a small amount.

Generally speaking, alloys for dental amalgams are composed of silver, tin and a small amount of copper and, when intermixed with mercury at about 1:1 weight ratio, have an amalgam structure of non-reacted alloy particles dispersed in an amalgam matrix produced by a reaction with mercury. This amalgam mass includes a silver-tin phase produced by reaction of silver and tin with mercury and a tin-mercury phase (GammaII) produced by a reaction of tin with mercury, which is weak mechanically and chemically. However, if tin is not added to a certain extent, the powdered alloy reacts insufficiently with mercury and, moreover, hardens quickly, so that not only is it inconvenient for use but also the silver-tin phase itself may become insufficient in strength.

However, it has been found that, if the powdered alloy contains a large amount of copper, tin reacts with copper to form $Cu_6Sn_5$, a stable intermetallic compound. Thus, the structure becomes such that relatively large particles of non-reacted alloy are surrounded by relatively small crystal grains of $Cu_6Sn_5$ with the remaining space filled with the amalgam matrix. This amalgam matrix is composed of a silver-mercury phase and includes substantially no tin-mercury phase which is chemically and mechanically weak.

The composition optimum to produce the intermetallic compound $Cu_6Sn_5$ consists of 1 part by weight of copper and 2 parts by weight tin. Accordingly, it is believed that most of the tin in the alloy is consumed for producing said intermetallic compound and for reinforcing the silver-tin phase, rather than for producing the mechanically and chemically weak tin-mercury phase. However, alloys containing over 6% copper by percentage weight have poor tarnish resistance.

Object of the Invention

It is the object of the invention to provide a group of alloys amalgamable with mercury for dental amalgams which possess superior physical and mechanical properties and tarnish resistance at the same time.

SUMMARY OF THE INVENTION

The powdered alloys according to this invention have, in weight percentages, 20% and above silver, 20 to 50% tin, 9.5 to 50% copper, and 0.5% and above indium. A preferred copper content is between 10% and 35% and especially between 11% and 20%. The most preferred copper content is 13% ±0.5%. A preferred silver content is at least 40% by weight and especially at least 50% by weight. A preferred tin content is 20% to 40% by weight and especially 20% to 30% by weight. Finally, the preferred indium content is 0.5% to 10% by weight and especially between 3% and 6% by weight.

The abovementioned powdered alloys are then triturated with mercury to form an amalgam. Preferred dental amalgams consist by weight percentages of 18% to 35% silver, 11% to 16% tin, 6% to 15% copper, 1% to 5% indium and the balance mercury at the time of trituration. The trituration is effected at a weight ratio of 1 part alloy powder to 0.82–1.0 part mercury.

In the above composition, silver content less than 20% makes amalgamation with mercury difficult, acccompanied by slow hardening speed. Tin content less than 20% makes amalgamation with mercury difficult with too rapid hardening speed, while more than 50% tin results in large aging contraction and slow hardening speed. Copper content of 9.1% or less comes in the technical range of the above-mentioned Japanese patent specification and, moreover, is insufficient to prevent the tin-mercury phase in the amalgam, while more than 50% copper makes amalgamation with mercury difficult with slow hardening speed due to consequent reduction in the silver and tin contents. Indium content of less than 0.5% gives insufficient protection against discoloration.

This invention will be further described hereinunder with reference to some practical examples in order to facilitate understanding.

EXAMPLE I

An alloy consisting in weight percentage of 60% silver, 24% tin, 13% copper and 3% indium was atomized and heat-treated, and one part by weight of the resultant powdered alloy was triturated with 0.82 part by weight of mercury for 15-seconds. All trituration described herein was made in the Standard Shofu Capsule, using the Shofu Amalgam Mixer Deluxe operating at 100 VAC 50 Hz. The properties were then measured as follows:

| | |
|---|---|
| Hardening time: | 7 minutes |
| Mechanical and physical properties after 24 hours: | |
| Dimensional change: | +5.7 $\mu$/m |
| Flow: | 0.08% |
| Compressive strength: | 5494 Kg/cm$^2$ |
| Static creep: | 0.17% (measured 7 days after trituration with a load of 369 Kg/cm$^2$ applied for four hours and percent deformation was measured at the end of the first and fourth hours.) |
| Extent of tarnish was measured as follows: | |
| Luminosity: | 6/ (at chroma saturation 1 and hue 5Y according to the JIS Z 8721 standard color chart, after dipped in 0.1% sodium sulfide solution for 72 hours.) |

EXAMPLE II

An alloy consising in weight percentage of 48% silver, 30% tin, 18% copper and 4% indium was atomized and heat-treated, and one part by weight of the resultant powdered alloy was triturated with 0.82% part by weight of mercury for 15-seconds. The properties measured under the same conditions as in Example I were as follows:

| | |
|---|---|
| Hardening time: | 6 minutes |
| Mechanical properties after | 24 hours: |
| Dimensional change: | +4 $\mu$/cm |
| Flow: | 0.06% |
| Compressive strength: | 5640 Kg/cm$^2$ |
| Static creep: | 0.10% |
| Luminosity: | 6/ |

EXAMPLE III

An alloy consisting in weight percentage of 29% silver, 38% tin, 29% copper and 6% indium was atomized and heat-treated, and one part by weight of the resultant powdered alloy was triturated with 0.82 part by weight of mercury for 15-seconds. The properties thereof were measured under the same conditions as Example I and were as follows:

| | |
|---|---|
| Hardening time: | 8 minutes |
| Mechanical properties after | 24 hours: |
| Dimensional change: | +3 $\mu$/cm |
| Flow: | 0.13% |
| Compressive strength: | 5520 Kg/cm$^2$ |
| Static creep: | 0.11% |
| Luminosity: | 7/ |

EXAMPLE IV

An alloy consisting in weight percentage of 60% silver, 23% tin, 12% copper and 5% indium was atomized and heat-treated, and one part by weight of the resultant powdered alloy was triturated with 0.87 part by weight of mercury for 15-seconds. The properties were then measured under the same conditions as in Example I as follows:

| | |
|---|---|
| Hardening time: | 8 minutes |
| Mechanical properties after | 24 hours: |
| Dimensional change: | −1 $\mu$/cm |
| Flow: | 0.11% |
| Compressive strength: | 6303 Kg/cm$^2$ |
| Static creep: | 0.10% |
| Luminosity: | 7/ |

EXAMPLE V

An alloy consisting in weight percentage of 60% silver, 22% tin, 13% copper and 5% indium was atomized and heat-treated, and 1 part by weight of the resultant powdered alloy was triturated with 0.84 part by weight mercury for 15-seconds. The properties were then measured under the same conditions as in Example I as follows:

| | |
|---|---|
| Hardening time: | 7 minutes |
| Mechanical and physical properties after 24 hours: | |
| Dimensional changes: | 0 ± 2 $\mu$/cm |
| Flow: | 0.13% |
| Compressive strength: | 6099 Kg/cm$^2$ |
| Static creep: | 0.08% |
| Luminosity: | 7/ |

EXAMPLE VI

An alloy consisting in weight percentage of 55% silver, 27% tin, 13% copper and 5% indium was atomized and heat-treated, and one part by weight of the resultant powdered alloy was triturated with 0.9 part by weight of mercury for 15-seconds. The properties were then measured under the same conditions as in Example I as follows:

| | |
|---|---|
| Hardening time: | 8 minutes |
| Mechanical properties after | 24 hours: |
| Dimensional change: | −1.8 $\mu$/cm |
| Flow: | 0.23% |
| Compressive strength: | 5096 Kg/cm$^2$ |
| Static creep: | 0.23% |
| Luminosity: | 7/ |

EXAMPLE VII

An alloy consisting in weight percentage of 28.5% silver, 28.5% tin, 38% copper and 5% indium was atomized and heat-treated, and one part by weight of the resultant powdered alloy was triturated with one part by weight of mercury for 15-seconds. The properties were then measured under the same conditions as in Example I as follows:

| Hardening time: | 8 minutes |
|---|---|
| Mechanical and physical properties after 24 hours: | |
| Dimensional change: | −5.8 μ/cm |
| Flow: | 0.23% |
| Compressive strength: | 5553 Kg/cm$^2$ |
| Static creep: | 0.18% |
| Luminocity: | 6/ |

EXAMPLE VIII

An alloy consisting in weight percentage of 64% silver, 22% tin, 9.5% copper and 4.5% indium was atomized and heat-treated, and one part by weight of the resultant powdered alloy was triturated with 0.86 part by weight of mercury for 15 seconds. The properties were then measured under the same conditions as in Example I as follows:

| Hardening time: | 8 minutes |
|---|---|
| Mechanical and physical properties after 24 hours: | |
| Dimensional change: | −1.8 μ/cm |
| Flow: | 0.30% |
| Compressive strength: | 5420 Kg/cm$^2$ |
| Static Creep: | 0.20% |
| Luminocity: | 7/ |

In the above examples, the alloys were atomized into powder. Mechanical lathe-cutting may be used for powderizing. In the latter case, however, some deterioration in mechanical properties occur while tarnishability is unchanged. A small amount of zinc of about one percent by weight or less may be added for controlling oxidation of the alloys, or for facilitating the atomizing operation, or for controlling the negative dimensional change of the amalgams. However, it is undesirable to add a large amount of zinc, since the positive dimensional change may become too large. Some comparative references are given below for demonstrating the effect of this invention. In the following references, characteristics were measured under the same conditions as in Example I.

REFERENCE I

An alloy made according to the American Dental Association Specification No. 1 (Revised), containing by weight percentage of 69% silver, 28% tin, and 3% copper was lathe-cut to powder and the alloy was triturated with mercury on a 1:1 ratio by weight for 15-seconds. The properties were as follows:

| Mechanical properties after 24 hours: | |
|---|---|
| Dimensional change: | −5 to −9 μ/cm |
| Flow: | 2 to 3% |
| Compressive strength: | 3600 to 3900 Kg/cm$^2$ |
| Static Creep: | 1 to 4% |
| Luminosity: | 5/ |

REFERENCE II

The same alloy as in Reference I was atomized and the resultant particles were triturated with mercury on a 1:1 weight ratio for 12-seconds. The properties were as follows:

| Mechanical properties after 24 hours: | |
|---|---|
| Dimensional change: | −3 to −8 μ/cm |
| Flow: | 0.5 to 0.8% |
| Compressive strength: | 3900 to 4300 Kg/cm$^2$ |
| Static creep: | 0.5 to 0.8% |
| Luminosity: | 5/ |

REFERENCE III

A commercially-available powdered alloy embodying the teachings of said U.S. Pat. No. 3,305,356 was triturated with mercury on a 1:1 weight ratio for 25 seconds. The properties were as follows:

| Mechanical properties after 24 hours: | |
|---|---|
| Dimensional change: | +4 to +8 μ/cm |
| Flow: | 0.49 to 0.22% |
| Compressive strength: | 4200 to 5000 Kg/cm$^2$ |
| Static creep: | 0.2 to 0.3% |
| Luminosity: | 4/ |

As can be seen from the above comparison, the alloys for dental amalgam according to this invention are superior to prior art alloys in both mechanical and physical properties, and in tarnish resistance.

We claim:

1. An amalgamable alloy for a dental amalgam consisting essentially, by weight, of at least 50% silver, 20 to 30% tin, 3 to 6% indium and 11 to 20% copper, said copper being present in an amount sufficient to form the intermetallic compound $Cu_6Sn_5$ with the tin and to provide only minimal amounts of unalloyed tin to form the gamma-II phase upon amalgamation.

2. A dental alloy capable of amalgamation with mercury, which consists essentially, by weight, of about 60% silver, 22% tin, 13% copper and 5% indium.

3. An improved dental amalgam consisting in weight percentage of 18 to 35% silver, 11 to 16% tin, 6 to 15% copper, 1 to 5% indium, and the balance mercury at the time of trituration.

4. A dental alloy capable of amalgammation with mercury, which consists essentially, by weight, of about 60% silver, 23% tin, 12% copper and 5% indium.

* * * * *